(12) United States Patent
Krapf et al.

(10) Patent No.: US 9,726,779 B2
(45) Date of Patent: Aug. 8, 2017

(54) UWB MEASURING DEVICE

(75) Inventors: Reiner Krapf, Filderstadt (DE); Heiko Braun, Leonburg (DE)

(73) Assignee: Robert Bosch GmbH, Stuttgart (DE)

( * ) Notice: Subject to any disclaimer, the term of this patent is extended or adjusted under 35 U.S.C. 154(b) by 613 days.

(21) Appl. No.: 13/384,185

(22) PCT Filed: May 17, 2010

(86) PCT No.: PCT/EP2010/056721
§ 371 (c)(1),
(2), (4) Date: Mar. 23, 2012

(87) PCT Pub. No.: WO2011/006696
PCT Pub. Date: Jan. 20, 2011

(65) Prior Publication Data
US 2012/0182175 A1     Jul. 19, 2012

(30) Foreign Application Priority Data
Jul. 14, 2009   (DE) .................. 10 2009 027 666

(51) Int. Cl.
*G01V 3/12* (2006.01)
*G01S 13/02* (2006.01)
*G01N 22/04* (2006.01)
*G01S 13/88* (2006.01)

(52) U.S. Cl.
CPC ............ *G01V 3/12* (2013.01); *G01S 13/0209* (2013.01); *G01N 22/04* (2013.01); *G01S 13/888* (2013.01)

(58) Field of Classification Search
CPC .. G01S 13/888; G01S 13/887; G01S 13/0209; G01V 3/12; G01V 8/005; G01N 22/04; G01N 22/00

USPC ............................................. 342/22
See application file for complete search history.

(56) References Cited

U.S. PATENT DOCUMENTS

| 5,905,455 A * | 5/1999 | Heger et al. ............... 342/22 |
| 6,206,340 B1 * | 3/2001 | Paese et al. ........... 251/129.04 |
| 7,236,120 B2 * | 6/2007 | Healy et al. .............. 342/22 |
| 7,956,794 B2 * | 6/2011 | Skultety-Betz et al. ........ 342/22 |
| 8,493,076 B2 * | 7/2013 | Krapf et al. ............... 324/640 |
| 8,546,759 B2 * | 10/2013 | Skultety-Betz et al. . 250/339.05 |

(Continued)

FOREIGN PATENT DOCUMENTS

| DE | 10 2004 007 315 A1 | 8/2005 |
| DE | 10 2004 031 627 A1 | 2/2006 |
| DE | 10 2006 002 666 A1 | 7/2007 |

OTHER PUBLICATIONS

International Search Report corresponding to PCT Application No. PCT/EP2010/056721, mailed Sep. 1, 2010 (German and English language document) (7 pages).

*Primary Examiner* — Matthew M Barker
(74) *Attorney, Agent, or Firm* — Maginot, Moore & Beck LLP (57) ABSTRACT

A UWB measuring device, in particular a hand-held positioning device, includes at least one signal-generating unit for generating at least one first UWB measuring signal, which is intended for a UWB measurement. The signal-generating unit is provided for generating a second measuring signal that differs from the first UWB measuring signal in at least one signal parameter. The second measuring signal is intended to detect a distance from an examination object and/or contact with the examination object.

13 Claims, 4 Drawing Sheets

(56) References Cited

U.S. PATENT DOCUMENTS

| | | |
|---|---|---|
| 8,686,891 B2* | 4/2014 | Krapf et al. ................... 342/22 |
| 2004/0263383 A1* | 12/2004 | Sako ....................... G01S 13/32 |
| | | 342/118 |
| 2005/0179578 A1 | 8/2005 | Healy et al. |
| 2006/0061504 A1 | 3/2006 | Leach et al. |
| 2008/0036644 A1 | 2/2008 | Skultety-Betz et al. |
| 2008/0055149 A1* | 3/2008 | Rees et al. ..................... 342/29 |
| 2008/0148803 A1* | 6/2008 | Skultety-Betz et al. ....... 73/1.01 |
| 2008/0266544 A1* | 10/2008 | Wolf et al. ................... 356/5.01 |
| 2009/0262005 A1* | 10/2009 | McNeill et al. ................ 342/22 |
| 2010/0156391 A1* | 6/2010 | Krapf et al. ............... 324/76.19 |

* cited by examiner

UWB MEASURING DEVICE

This application is a 35 U.S.C. §371 National Stage Application of PCT/EP2010/056721, filed on May 17, 2010, which claims the benefit of priority to Serial No. DE 10 2009 027 666.1, filed on Jul. 14, 2009 in Germany, the disclosures of which are incorporated herein by reference in their entirety.

The disclosure relates to a UWB measuring device.

A UWB measuring device comprising a signal generating unit for generating a first UWB measuring signal is already known, the first UWB measuring signal being provided for a UWB measurement.

SUMMARY

The disclosure relates to a UWB measuring device, particularly a hand-held positioning device, comprising at least one signal generating unit for generating at least a first UWB measuring signal which is intended for a UWB measurement.

It is proposed that the signal generating unit is provided for generating a second measuring signal, different from the first UWB measuring signal in at least one signal parameter, which is intended for detecting a distance from an object to be examined and/or a contact with the object to be examined. In this context, "provided" is intended to be understood especially as specially configured and/or specially designed and/or specially programmed. Furthermore, a "UWB measuring signal" is intended to be understood to be an ultra-wideband signal, the ultra-wideband signal having a frequency spectrum with a center frequency and a frequency bandwidth of at least 500 MHz. The center frequency is preferably selected within a frequency range of from 1 GHz to 15 GHz. The UWB measurement is preferably provided for a positioning measurement, the UWB measuring signal being intended for detecting the presence of an object arranged in the object to be examined and/or for a moisture measurement, particularly a moisture content of the object to be examined, and/or for other UWB measurements appearing to the expert as being appropriate. Operating the UWB measurement with the first UWB measuring signal requires a license according to the guidelines of which, especially on the basis of safety and/or a faultless operation of other radio services, the operation is only allowed to take place in the case of a contact of the UWB measuring device with the object to be examined, such as, particularly, a wall surface. For this purpose, an operation with the second measuring signal can preferably be carried out without a license so that, in particular, a measuring operation with the second measuring signal can be started with a distance of the positioning device from the object to be examined. Furthermore, a "signal parameter" is intended to be understood to be, in particular, a power of the emitted signal and/or a frequency and/or a pulse sequence of the emitted signal and/or other parameters appearing to the expert as being appropriate. In this context a "contact with the object to be examined" is intended to be understood to be, in particular, a direct contact of the UWB measuring device, particularly of a carriage for moving the UWB measuring device on a surface of the object to be examined and/or a sliding face for sliding the UWB measuring device on the surface of the object to be examined. "Distance from the object to be examined" is intended to be understood to be, in particular, a shortest distance between the UWB measuring device, especially of a surface which is provided for emitting the first UWB measuring signal and/or the second measuring signal, and the object to be examined. In this context, a measurement of the distance from the object to be examined is preferably carried out by means of a measurement of a phase difference between a phase of a reference signal, for example of the second measuring signal emitted by the UWB measuring device, and a phase of the second measuring signal reflected from a surface of the object to be examined. In principle, other signal parameters, appearing to the expert as being appropriate, of the second measuring signal can also be utilized for determining and/or measuring the distance of the UWB measuring device from the object to be examined, such as, for example, a measurement of an amplitude of the second measuring signal. By means of the embodiment of the UWB measuring device according to the disclosure, an increased reliability of the UWB measuring device can be advantageously achieved in that the operation with a UWB measurement can be restricted to a dwell period of a contact of the UWB measuring device with the object to be examined. In addition, high operator friendliness can be achieved in that, for example, in the case of a wall contact, a UWB measurement occurs automatically and thus, for example, operating errors by the operator are advantageously prevented.

In principle, the UWB measuring device can be formed by all measuring devices appearing to the expert as being appropriate. Due to the advantageous embodiment for detecting a distance and/or a contact with the object to be examined, the UWB measuring device is particularly advantageously constructed as positioning device and/or moisture measuring device.

The second measuring signal is particularly advantageously formed at least partially by a UWB measuring signal. In this context, the second measuring signal is advantageously used, particularly emitted and/or received, in a special frequency range as are common, for example, in UWB communication devices, a frequency of the second UWB measuring signal preferably being arranged within a frequency range of between 6 GHz and 8.5 GHz. In this frequency range, a measuring operation with the second UWB measuring signal can occur particularly advantageously without restriction, especially without license so that an existing contact between the UWB measuring device and a surface of the object to be examined is not a prerequisite for the measuring operation. In this context, a common signal source can be advantageously used for the first UWB measuring signal and the second UWB measuring signal so that a particularly compact and particularly cost-effective UWB measuring device can be provided.

It is also proposed that the second measuring signal is formed at least partially by a narrow-band measuring signal. In this context, a "narrow-band measuring signal" is a signal for transmitting information and/or services within a limited frequency band. The narrow-band measuring signal is formed by an ISM measuring signal. An "ISM signal" is a signal that is emitted within a range of at least one ISM band, an "ISM band" being understood to be, in particular, frequency ranges which can be used by radio-frequency devices, especially in domestic and/or medical areas. An emission of the narrow-band measuring signal in the measuring device is preferably free of license or only needs a general license so that the emission of the narrow-band measuring signal does not impose a restriction such as, for example, of a contact with the surface of the object to be examined. The narrow-band measuring signal emitted by the UWB measuring device can also be formed by a single signal having a narrow-band transmit frequency, or by several signals having in each case a narrow-band transmit frequency formed differently from the other signals. This embodiment of the invention makes it possible that the narrow-band measuring signal, especially the ISM measuring signal can be advantageously emitted temporally or locally before a contact of the UWB measuring device with the surface of the object to be examined. In addition, when using the transmit signal having several different transmit frequencies, a high probability of recognition and/or a high measuring accuracy of the UWB measuring device can be advantageously achieved. Thus, faulty operation of the UWB measuring device with the first UWB measuring signal can be advantageously prevented, in particular.

In an alternative development of the disclosure, it is proposed that the signal generating unit has at least one signal source which is intended for generating the first UWB measuring signal and the second measuring signal. In this context, a "signal source" is intended to be understood especially to be a unit and/or an element which is intended for generating the first UWB measuring signal and the second measuring signal. In this context, a particularly compact UWB measuring device can be produced by saving, in particular, further components, installation space, assembly complexity and costs.

As an alternative, it is proposed that the signal generating unit have a first signal source for generating the first UWB measuring signal and at least one second signal source for generating the second measuring signal. An advantageous signal separation can be achieved between the first UWB measuring signal and the second measuring signal and an unwanted superposition and/or disturbance between the two measuring signals can be prevented, in particular.

The UWB measuring device advantageously has at least one signal filter element which is intended for a signal selection of the first UWB measuring signal and/or the second measuring signal. In this context, a "signal filter element" is intended to be understood, in particular, to be an element which is formed at least partially by a high-pass element and/or a low-pass element and/or a band pass element. When using a common signal source for the first UWB measuring signal and the second measuring signal such as, for example, a signal source for an ultra-wideband signal, the first UWB measuring signal or the second measuring signal can be adapted to respective transmitting conditions. In addition, the signal of a single signal source can be converted into two mutually different measuring signals in a constructionally simple manner.

Furthermore, it is proposed that the UWB measuring device have an antenna element which is intended for emitting and/or receiving the first UWB measuring signal and the second measuring signal, as a result of which further components, constructional space, assembly complexity and costs can be advantageously saved. In this context, "emitting" is intended to be understood especially as radiation of the first and the second measuring signal.

As an alternative, it is proposed that the UWB measuring device have a first antenna element which is intended for emitting and/or receiving the first UWB measuring signal, and a second antenna element which is intended for emitting and/or receiving the second measuring signal, as a result of which unwanted interference and/or superposition of the two measuring signals can be advantageously prevented. In addition, further filter elements which are required with a common antenna element and follow the latter for separating the two measuring signals can be omitted at least partially from this arrangement. The first antenna element is preferably formed in this context by an ultra-wideband antenna element and the second antenna element is preferably formed by an antenna element for emitting and/or receiving narrow-band measuring signals or by an ultra-wideband antenna element.

The UWB measuring device exhibits particularly advantageously at least one signal switching element which is intended for switching between an operating mode using the first UWB measuring signal and an operating mode using the second measuring signal. In this context, a measuring operation can be advantageously adapted to a current positioning of the UWB measuring device with respect to the object to be examined. In addition, a constructionally simple switching can be achieved in this context. The signal switching element is also preferably intended for switching, in the operating mode with the first UWB measuring signal, at the same time, into the operating mode with the second measuring signal and vice versa, so that both operating modes can take place at least partially at the same time.

In an alternative development of the disclosure, it is proposed that the UWB measuring device have a computing unit which is intended for an at least partially automatic switching between the operating mode using the first UWB measuring signal and the operating mode using the second measuring signal by means of the signal switching element. In this context, a "computing unit" is intended to be understood specially to be a unit which can be formed by an evaluating unit and/or a signal processing unit, where the computing unit can be formed both by a processor on its own and especially by a processor and further electronic components such as, for example, a storage means. Furthermore, at least one operating program can be stored in the computing unit. Furthermore, "automatic" is intended to be understood especially to be an automated and/or automatic switching so that manual operating errors can be advantageously prevented during a switching process. By means of the embodiment according to the disclosure, switching and/or selection of the operating modes adapted to an instantaneous and/or current measuring position and/or measuring situation of the UWB measuring device can be achieved.

Furthermore, it is proposed that the UWB measuring device have a computing unit which is intended for modulating the second measuring signal during the detection of the distance from the object to be examined and/or of the contact with the object to be examined. In this context, "modulating the second measuring signal" is intended to be understood to be, in particular, a change of the second measuring signal, wherein the second measuring signal can here be changed and/or modulated with regard to its amplitude and/or especially advantageously with regard to its frequency. By "during" it is intended to be understood, in particular, that the detection of the distance of the UWB measuring device from the object to be examined and the modulation of the second measuring signal can occur at the same time. In this context, it is possible to reduce and/or prevent, in particular, disturbances within the frequency range of the second measuring signal by other signal-emitting devices. In addition, an interference-free and precise measuring of the distance of the UWB measuring device from the object to be examined can be achieved particularly advantageously.

In addition, it is proposed that the UWB measuring device have a computing unit which is intended for activating the operating mode using the first UWB measuring signal in the case of the presence of a contact with the object to be examined. In this context, "activate" is intended to be understood to be, in particular, starting and/or beginning with the operating mode with the first UWB measuring signal. In this context, in particular, a safety risk for the operator of the UWB measuring device can be minimized in that a decision is made by the computing unit whether and when there is a contact of the UWB measuring device with the object to be examined.

In addition, the disclosure is based on a UWB measuring process for a UWB measuring device, particularly a hand-held positioning device, wherein a UWB measurement is effected using a first UWB measuring signal and a detection of a distance of the UWB measuring device from an object to be examined and/or a measurement of a contact of the UWB measuring device with the object to be examined is effected using a second measuring signal.

BRIEF DESCRIPTION OF THE DRAWINGS

Further advantages are obtained from the following description of the drawing. In the drawing, exemplary embodiments of the disclosure are represented. The description and the claims contain numerous features in combination. The expert will also suitably consider the features individually and combine them in appropriate further combinations.

DETAILED DESCRIPTION

Figure 1:
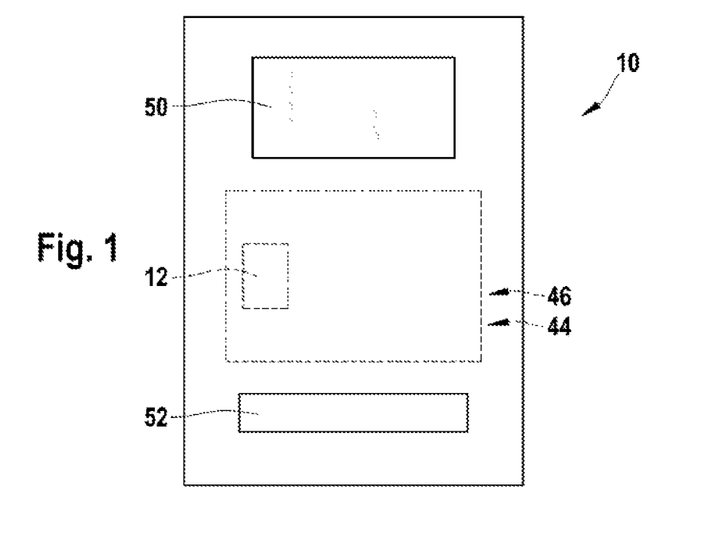
FIG. 1 shows a UWB measuring device according to the disclosure, constructed as a positioning device, in a diagrammatic representation.
Figure 2:
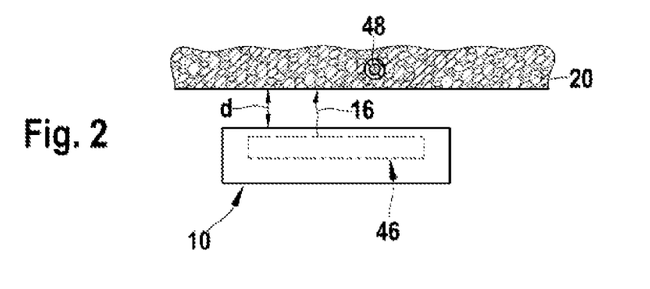
FIG. 2 shows the positioning device of FIG. 1 together with an object to be examined, in a top view.

FIG. 1 diagrammatically shows a UWB measuring device 10 according to the disclosure, constructed as a hand-held positioning device. The positioning device exhibits a positioning unit 46, formed by a UWB measuring unit 44, which exhibits a signal generating unit 12 for generating a first UWB measuring signal 14 which is intended for a positioning measurement, formed by a UWB measuring measurement, for detecting the presence of an object 48 arranged in an object to be examined 20, when operating the positioning unit 46. The hand-held positioning device also exhibits a display unit 50 for a visual output of a measurement result for an operator of the positioning device and an input unit 52 for an input of possible operating parameters and/or for switching the positioning device on or off by the operator. In FIG. 2, the positioning device is shown together with the object to be examined 20 which is formed here by a wall in a top view.

The signal generating unit 12 is also provided for generating a second measuring signal 16 different from the first UWB measuring signal 14 in at least one signal parameter, which second measuring signal is intended for detecting a distance d of the positioning device from the object to be examined 20, especially from one of the wall surfaces, and/or for detecting a contact with the object to be examined 20 (FIG. 2).

Figure 3:
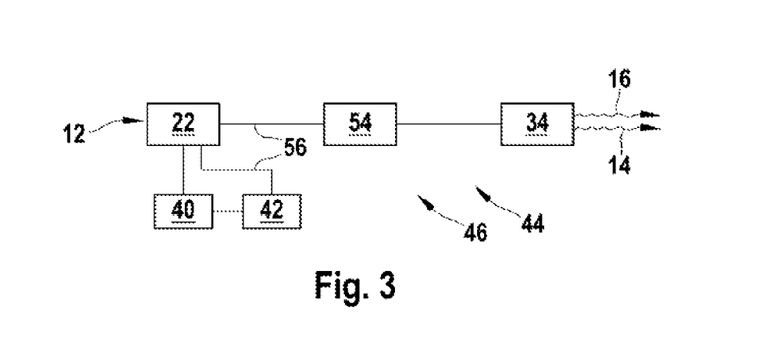
FIG. 3 shows a diagrammatic structure of a positioning unit of the positioning device comprising a common signal source with stepped frequency passes of the measuring signals.

FIG. 3 shows a first exemplary embodiment of the positioning unit 46 in greater detail. In this context, the signal generating unit 12 exhibits a single signal source 22 which is intended both for generating the first UWB measuring signal 14 and the second measuring signal 16. The second measuring signal 16 is here formed by a narrow-band ISM measuring signal, wherein the positioning device can be operated free of license by means of the narrow-band measuring signal. In addition, the positioning unit 46 has a single antenna element 34 which is intended for emitting and/or for receiving the first UWB measuring signal 14 and the narrow-band ISM measuring signal. The narrow-band ISM measuring signal can here be formed by a signal with a narrow-band frequency or by several signals having an in each case different narrow-band frequency. The signal source 22 is intended for emitting narrow-band measuring signals, the first UWB measuring signal 14 being emitted by means of the signal source 22 in that the narrow-band signal of the signal source generates a bandwidth of the first UWB measuring signal 14 by fast frequency passes (sweeps) of narrow-band frequency ranges of the signal.

The narrow-band ISM measuring signal can also exhibit a transmit power which is formed differently from a transmit power of the first UWB measuring signal 14. For example, a transmit power which is lower than the first UWB measuring signal 14 can be used for the narrow-band ISM measuring signal in order to operate the positioning device at least partially in an energy saving mode. Furthermore, for example, for achieving a high detection rate of the object to be examined 20, especially of the wall surface and/or of a distance d from the wall surface, a high output power of the narrow-band ISM measuring signal can be used.

Furthermore, the positioning unit 46 exhibits at least one signal switching element 40 which is intended for switching between an operating mode comprising the first UWB measuring signal 14 and an operating mode comprising the narrow-band ISM measuring signal. In addition, the positioning unit 46 exhibits a computing unit 42 which is intended for controlling the signal switching element 40, so that an at least partially automatic switching between the two operating modes and/or between the two transmit paths is provided for by means of the signal switching element 40. The computing unit 42 is also provided for controlling the signal generating unit 12 so that the emitting and/or receiving of the two measuring signals 14, 16, especially a temporal sequence of the emitting and/or receiving of the two measuring signals 14, 16, is controlled by the computing unit 42. By means of the computing unit 42, an alternating emitting and/or receiving of the first UWB measuring signal 14 and of the narrow-band ISM measuring signal or a simultaneous emitting and/or receiving of the first UWB measuring signal 14 and of the narrow-band ISM measuring signal can be achieved in this context. In addition, the computing unit 42 is here intended for modulating a transmit frequency of the second measuring signal 16.

In an alternative embodiment of the disclosure, the signal switching element 40 and the computing unit 42 can be constructed as one piece.

The individual components and units of the positioning unit 46 are connected to one another by means of a data transmission element 56. The signal generating unit 12 together with the further signal processing elements 54, the antenna element 34 and the computing unit 42 are integrated in one ASIC (application specific indicated circuit). In principle, however, it is also conceivable that the individual elements are constructed and/or arranged as discrete elements.

At the beginning of an operation of the positioning device, a contact of the positioning device with the object to be examined 20 and/or a distance d between the object to be examined 20 and the positioning device is initially detected. In this process, the narrow-band ISM measuring signal is emitted by the signal generating unit 12, controlled by the computing unit 42, a measurement of the distance d being effected advantageously via a measurement of a phase difference 4 between the narrow-band ISM measuring signal emitted and a narrow-band signal reflected from the surface of the object to be examined 20. In this context, the distance d is calculated as: $d=\Delta\phi \cdot c_0/(4\pi \cdot f)$, where f is the measuring frequency and $c_0$ the velocity of light. In this context, a range of unambiguity $d_g$ of the distance measurement is $d_g = c_0/(2f)$, depending on frequency, wherein only distances d between the unambiguity range $d_g$ and an integral multiple of the unambiguity range $n \cdot d_g$ can be differentiated, n representing an integral positive number. A distance d from the unambiguity range $d_g$ or an integral multiple thereof can no longer be differentiated due to the principle of measurement. To increase an accuracy of measuring the distance d between the positioning device and the object to be examined 20, the signal generating unit 12 emits at least two narrow-band ISM measuring signals having in each case different measuring frequencies, the measuring frequencies and/or the different narrow-band ISM measuring signals being modulated by means of the computing unit 42. In this process, the measuring frequencies of the narrow-band ISM measuring signal are modulated during the distance measurement and/or the contact detection. As an alternative, the distance d of the positioning device from the object to be examined could be detected by means of a detection of an amplitude of the narrow-band ISM measuring signal and an amplitude of the reflected narrow-band signal.

In contrast to an operating mode using the first UWB measuring signal 14, an operating mode using the narrow-band ISM measuring signal can be operated free of license so that, in particular, a measuring operation in the operating mode using the narrow-band ISM measuring signal can be effected at a distance of the positioning device from the object to be examined 20 whereas an operating mode using the first UWB measuring signal 14 can only be effected in the case of a contact of the positioning device with the object to be examined 20 due to licensing restrictions.

As soon as a contact of the positioning device with the object to be examined 20 is detected during operation of the positioning device, the operating mode using the first UWB measuring signal 14 for a positioning measurement is activated automatically by the computing unit 42. In an alternative embodiment of the disclosure, it is also conceivable that an item of information indicating a contact of the positioning device with the object to be examined 20 is output for the operator via the display unit 50 and the operator switches manually into the operating mode comprising the first UWB measuring signal 14. The operating mode of the narrow-band ISM measuring signal still remains activated so that, after the emission of one or more UWB measuring signals 14, one or more narrow-band ISM measuring signals are emitted in order to control an establishment of the contact of the positioning device with the object to be examined 20. By means of the computing unit 42 and the simultaneously operated operating modes using the first UWB measuring signal 14 and the narrow-band ISM measuring signal, a lifting-away of the positioning device from the object to be examined 20 can be independently detected and the operating mode using the first UWB measuring signal 14 can be automatically interrupted or switched off thereupon for safety reasons.

The first UWB measuring signal 14 exhibits a first direction of polarization and the narrow-band ISM measuring signal exhibits a second direction of polarization, the two directions of polarization being essentially aligned orthogonally with respect to one another so that a mutual interference of the two measuring signals 14, 16 in the case of a simultaneous emission and/or reception of the measuring signals 14, 16 is minimized. In principle, it is conceivable at any time that the two directions of polarization are essentially aligned in parallel with one another.

In addition, the positioning unit 46 has one or more signal processing elements 54 which is or are aligned along a signal path between the signal generating unit and the antenna element 34. At least one signal processing element 54 can be formed by a transceiver which is intended for compensating for signal fluctuations of the first UWB measuring signal 14 and/or the narrow-band ISM measuring signal, the measuring signals 14, 16 in this case being conducted to a device-internal reference network. In this context, a separate transceiver can be available for each of the two measuring signals 14, 16, or a transceiver to which both measuring signals 14, 16 are conducted and a switching between the two measuring signals 14, 16 is effected by means of a switching element.

In FIGS. 4 to 8b, embodiments of a UWB measuring device 10 which are alternative to FIG. 3, are shown. In principle, components, features and functions essentially remaining identical are numbered with identical reference symbols. To distinguish between the exemplary embodiments, the letters a to e have been added to the reference symbols of the following exemplary embodiment. The subsequent description is essentially restricted to the differences from the exemplary embodiment in FIGS. 1 to 3, it being possible to refer to the description of the exemplary embodiment in FIGS. 1 to 3 with respect to components, features and functions remaining identical.

Figure 4:
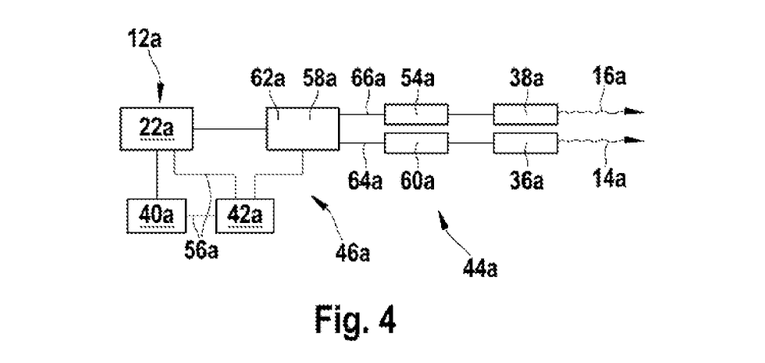
FIG. 4 shows a structure of the positioning unit which is an alternative to FIG. 3, FIGS. 5a, 5b show a diagrammatic structure of the positioning device comprising a signal filter element.

Compared with the positioning unit 46 in FIG. 3, a positioning unit 46a in FIG. 4 has two antenna elements 36a, 38a, a first antenna element 36a being intended for emitting and/or receiving a first UWB measuring signal 14a and the second antenna element 38a being intended for emitting and/or receiving a second measuring signal 16a which is formed by a narrow-band ISM measuring signal. In addition, the positioning unit 46a exhibits a number of signal processing elements 54a, 58a, 60a which are arranged along a signal path between a signal generating unit 12a and the two antenna elements 36a, 38a. A first signal processing element 58a is formed by a signal switching element 62a which is intended for switching between an operating mode using the first UWB measuring signal 14a and an operating mode using the narrow-band ISM measuring signal. The switching element 62a can be formed, for example, by a switchable diplexer which connects or disconnects a signal path 66a of the narrow-band ISM measuring signal. The signal switching element 62a is controlled by a computing unit 42a of the positioning unit 46a so that a signal path 64a, 66a is selected for the measuring signal 14a, 16a in dependence on the measuring signal 14a, 16a emitted by the signal generating signal unit 12a.

Figure 5A:
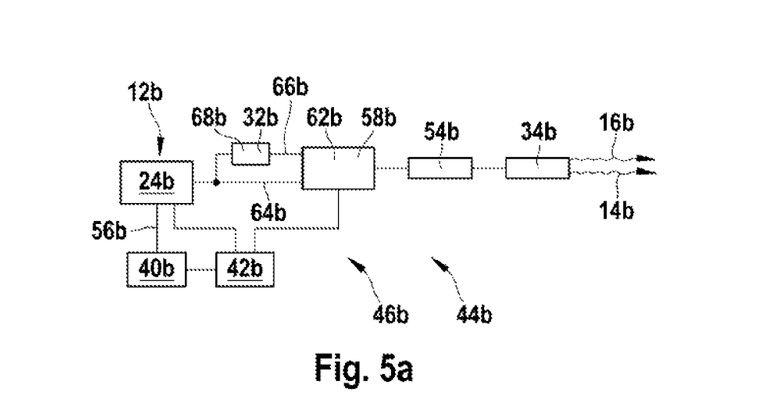
Figure 5B:
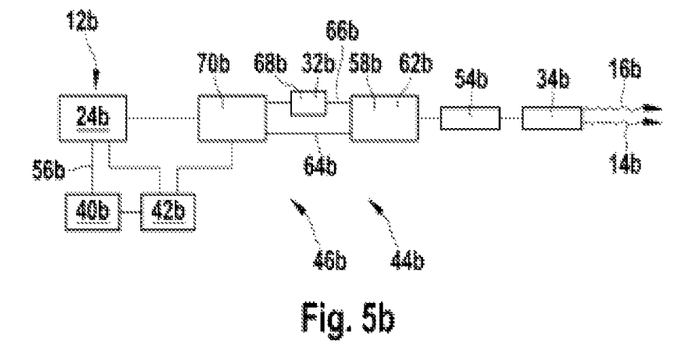

In FIGS. 5a and 5b, a further exemplary embodiment of a positioning unit 46b of the UWB measuring device 10 is shown. The positioning unit 46b has a signal generating unit 12b comprising a signal source 24b which is intended for emitting a first UWB measuring signal 14b. The signal source 24b in this arrangement is formed by a UWB signal source. Between the signal generating unit 12b and an antenna element 34b, a number of signal processing elements 54b, 58b, 68b of the positioning unit 46b are arranged. A first signal processing element 68b is formed by a signal filter element 32b which is arranged following the signal generating unit 12b. The signal filter element 32b is intended for a signal selection between the first UWB measuring signal 14b and a second measuring signal 16b, the signal filter element 32b being switched to conduct for the second measuring signal 16b and forming a barrier for the first UWB measuring signal 14b. In this arrangement, the second measuring signal 16b is formed by a narrow-band ISM measuring signal and/or a license-free broadband UWB measuring signal, the second UWB measuring signal in this arrangement being arranged within a frequency range of from 6 GHz to 8.5 GHz. The signal generated by the signal generating unit 12b is divided before the signal filter element 32b. The signal filter element 32b can be formed at least partially by a high-pass element, a low-pass element and/or a band pass element, the signal filter element 32b being arranged in the signal path 66b of the narrow-band ISM measuring signal. In principle, the signal filter element 32b could be provided for filtering the first UWB measuring signal 14b in an alternative embodiment.

The second signal processing element 58b which is arranged along a signal path between the signal generating unit 12b and the antenna element 34b is formed by a signal switching element 62b which is intended for switching between an operating mode using the first UWB measuring signal 14b and an operating mode using the second measuring signal 16b. The signal switching element 62b can be formed, for example, by a switchable diplexer which connects or disconnects a signal path 66b of the second measuring signal 16b. The positioning unit 46b also exhibits a computing unit 42b which is intended for controlling the signal switching element 62b so that an at least partially automatic switching between the two operating modes and/or between the two signal paths 64b, 66b is provided for by means of the signal switching element 62b. The computing unit 42b is also intended for controlling the signal generating unit 12b so that the emitting and/or receiving of the two measuring signals 14b, 16b, especially a temporal sequence of the emitting and/or receiving of the two measuring signals 14b, 16b is controlled. In this arrangement, an alternating emitting and/or receiving of the two measuring signals 14b, 16b or a simultaneous emitting and/or receiving of the two measuring signals 14b, 16b can be achieved by means of the computing unit 42b.

In FIG. 5b, a signal divider 70b is arranged preceding the signal filter element 32b for dividing the signals.

Figure 6:
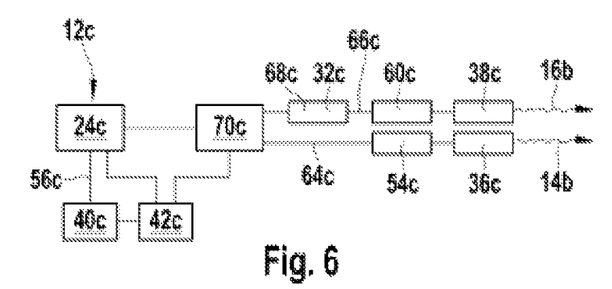
FIG. 6 shows a diagrammatic structure of the positioning device with a common signal source and two antenna elements.

FIG. 6 shows a further exemplary embodiment of the positioning unit 46. The positioning unit 46c exhibits two antenna elements 36c, 38c, the first antenna element 36c being intended for emitting and/or receiving the first UWB measuring signal 14c and the second antenna element 38c being intended for emitting and/or receiving the second measuring signal 16c. Starting from a signal divider 70c, the positioning unit 46c exhibits two signal paths 64c, 66c having in each case one antenna element 36c, 38c. An operating mode and a further structure of the positioning unit 46c correspond to an operating mode and a structure of the positioning unit 46b from FIG. 5b.

Figure 7A:
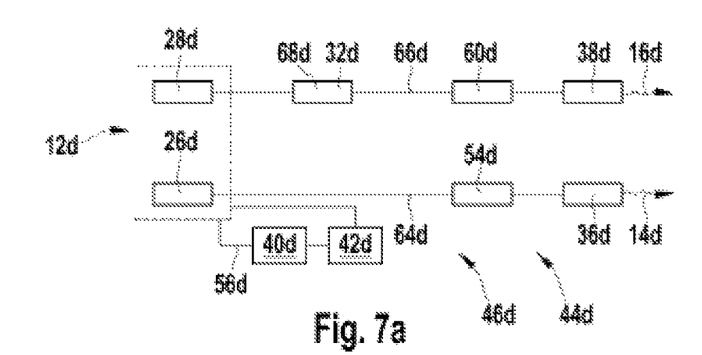
FIGS. 7a, 7b show a diagrammatic structure of the positioning device comprising two signal sources formed by in each case one ultra-wideband signal source.
Figure 7B:
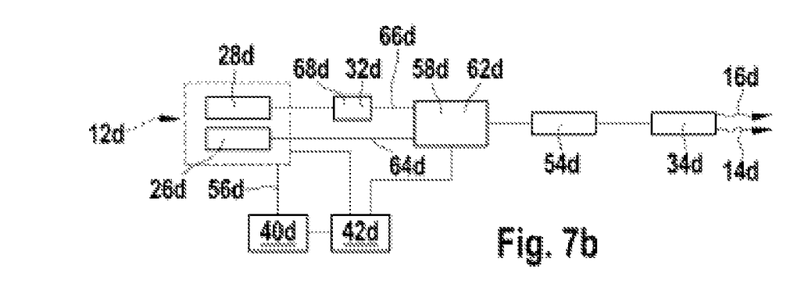

In FIGS. 7a and 7b, a further exemplary embodiment of the positioning unit 46d is in each case shown comprising a signal generating unit 12d which has two signal sources 26d, 28d. The two signal sources 26d, 28d are in each case formed by a UWB signal source.

In FIG. 7a, a positioning unit 46d has two antenna elements 36d, 38d so that a separate signal path 64d, 66d from the signal generating unit 12d to the antenna element 36d, 38d is available for each of the two measuring signals 14d, 16d. The signal path 66d of the second measuring signal 16d also has a signal filter element 32d. The second measuring signal 16d is configured analogously to the second measuring signal in FIGS. 5a to 6. A mode of action of the positioning unit 46d corresponds to a mode of action of the positioning units in FIGS. 5a to 6.

The exemplary embodiment in FIG. 7b exhibits a common antenna element 34d via which both the first UWB measuring signal 14d and the second measuring signal 16d are emitted and/or received. For this purpose, the positioning apparatus exhibits a signal switching element 62d which combines the two signal paths 64d, 66d and in addition passes the measuring signal 14d, 16d intended for measuring, depending on operating mode.

Figure 8A:
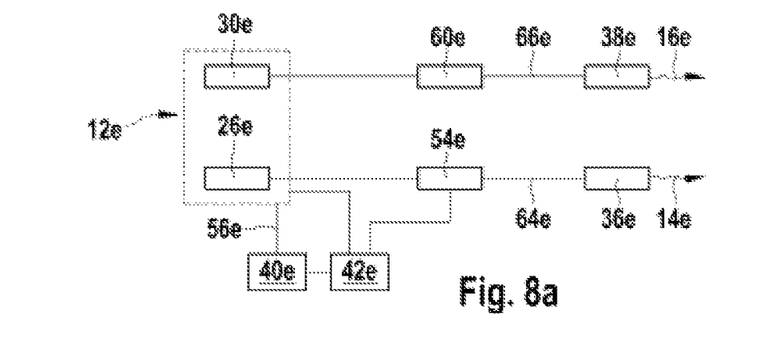
FIGS. 8a, 8b show a diagrammatic structure of the positioning device comprising an ISM signal source and an ultra-wideband signal source.
Figure 8B:
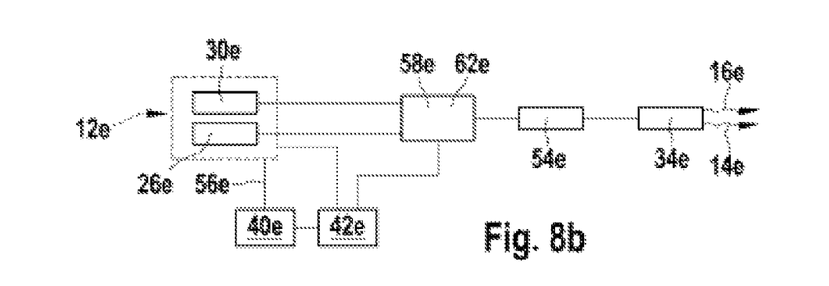

The exemplary embodiments in FIGS. 8a and 8b also exhibit in each case a signal generating unit 12e which comprises two signal sources 26e, 30e. The first signal source 26e is formed by a UWB signal source and is intended for emitting a first UWB measuring signal 14e. The second signal source 30e is formed by an ISM signal source and is intended for emitting a narrow-band ISM measuring signal. A further structure and an operating mode of the positioning unit 46e in this case corresponds to a structure and an operating mode of the positioning unit 46d in FIGS. 7a and 7b.

The invention claimed is:

1. An ultra wideband (UWB) measuring device, comprising
a signal generating unit configured to generate:
a first UWB measuring signal for a UWB measurement; and
a second measuring signal, different from the first UWB measuring signal in at least one signal parameter, the second measuring signal being formed at least partially by a narrow-band measuring signal; and
a computing unit operatively connected to the signal generating unit, the computing unit configured to:
detect a distance from a surface of an object to be examined and operate the signal generating unit to prevent emission of the first UWB measuring signal in response to the second measuring signal reflected from the surface indicating that the UWB measuring device is not in contact with the surface; and
detect contact with the surface of the object to be examined in response to the second measuring signal reflected from the surface of the object to be examined indicating that the UWB measuring device is in contact with the surface and operate the signal generating unit to emit the first UWB measuring signal in response to detecting contact with the surface of the object to be examined,
wherein the computing unit is further configured to activate an operating mode using the first UWB measuring signal in response to the UWB measuring device detecting contact with the surface of the object to be examined.

2. The UWB measuring device as claimed in claim 1, wherein the signal generating unit includes a single signal source configured to generate both the first UWB measuring signal and the second measuring signal.

3. The UWB measuring device as claimed in claim 1, the signal generating unit further comprising:
   a first signal source configured to generate the first UWB measuring signal; and
   a second signal source configured to generate the second measuring signal.

4. The UWB measuring device as claimed in claim 1, further comprising:
   at least one signal filter element configured to select at least one of the first UWB measuring signal and the second measuring signal.

5. The UWB measuring device as claimed in claim 1, further comprising:
   an antenna element configured to at least one of emit and receive the first UWB measuring signal and the second measuring signal.

6. The UWB measuring device as claimed in claim 1, further comprising:
   a first antenna element configured to at least one of emit and receive the first UWB measuring signal, and a second antenna element configured to at least one of emit and receive the second measuring signal.

7. The UWB measuring device as claimed in claim 1, further comprising:
   at least one signal switching element configured to switch between an operating mode using the first UWB measuring signal and an operating mode using the second measuring signal.

8. The UWB measuring device as claimed in claim 7, the computing unit being further configured to:
   at least partially automatically switch between the operating mode using the first UWB measuring signal and the operating mode using the second measuring signal by use of the at least one signal switching element.

9. The UWB measuring device as claimed in claim 1, the computing unit being further configured to:
   modulate the second measuring signal during the detection of the distance from the surface of the object to be examined and the detection of the contact with the surface of the object to be examined.

10. A method comprising:
   generating with using a signal generating unit a first ultra wideband (UWB) measuring signal intended for a UWB measurement;
   generating with the signal generating unit a second measuring signal different from the first UWB measuring signal in at least one signal parameter, the second measuring signals being formed at least partially by a narrow-band measuring signal;
   detecting with a computing unit operatively connected to the signal generating unit contact with a surface of the object to be examined using the second measuring signal reflected from the surface of the object to be examined;
   operating with the computing unit the signal generating unit to prevent emission of the first UWB measuring signal in response to the second measuring signal indicating the UWB measurement device is not in contact with the surface of the object to be examined; and
   operating with the computing unit the signal generating unit to emit the first UWB measuring signal in response to the second measuring signal indicating the UWB measurement device is in contact with the surface of the object to be examined.

11. The method of claim 10, wherein detecting the contact with the surface further comprises:
   emitting with the signal generating unit the second measuring signal;
   receiving with the signal generating device a reflected signal, the reflected signal is the second measuring signal reflected from the surface of the object to be examined; and
   detecting with the computing unit a distance to the surface of the object to be examined with reference to a phase difference between the second measuring signal and the reflected signal.

12. The method of claim 10, the generation of the first UWB measuring signal and the second measuring signal further comprising:
   generating the first UWB measuring signal with a first signal source in the signal generating unit; and
   generating the second measuring signal with a second signal source in the signal generating unit.

13. The method of claim 10, further comprising at least one signal filter element configured to select at least one of the first UWB measuring signal and the second measuring signal.

* * * * *